US010007753B2

(12) United States Patent
Leong

(10) Patent No.: US 10,007,753 B2
(45) Date of Patent: Jun. 26, 2018

(54) METHODS AND SYSTEMS FOR DETERMINING META-GENOTYPES

(71) Applicant: LIFE TECHNOLOGIES CORPORATION, Carlsbad, CA (US)

(72) Inventor: Harrison Leong, San Francisco, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days. days.

(21) Appl. No.: 14/759,496

(22) PCT Filed: Jan. 8, 2014

(86) PCT No.: PCT/US2014/010735
§ 371 (c)(1),
(2) Date: Jul. 7, 2015

(87) PCT Pub. No.: WO2014/110172
PCT Pub. Date: Jul. 17, 2014

(65) Prior Publication Data
US 2015/0356241 A1    Dec. 10, 2015

Related U.S. Application Data

(60) Provisional application No. 61/750,209, filed on Jan. 8, 2013.

(51) Int. Cl.
| | |
|---|---|
| G01N 33/48 | (2006.01) |
| G06F 19/18 | (2011.01) |
| G01N 33/49 | (2006.01) |
| G06F 19/28 | (2011.01) |
| G06G 7/58 | (2006.01) |

(52) U.S. Cl.
CPC ............. *G06F 19/18* (2013.01); *G01N 33/49* (2013.01); *G06F 19/28* (2013.01)

(58) Field of Classification Search
CPC .......... G06F 19/18; G06F 19/22; G06F 19/24; G06F 19/28
See application file for complete search history.

(56) References Cited

U.S. PATENT DOCUMENTS

| | | | |
|---|---|---|---|
| 2002/0091664 A1 | 7/2002 | Larder et al. | |
| 2007/0093968 A1 | 4/2007 | Zhang et al. | |
| 2010/0068710 A1 | 3/2010 | Buela et al. | |

OTHER PUBLICATIONS

Hashmi, Ghazala, et al., "Determination of 24 Minor Red Blood Cell Antigens for More Than 2000 Blood Donors by High-Throughput DNA Analysis", *Transfusion*, vol. 47, No. 4, Apr. 2007, 736-747.
Hashmi, Ghazala, "Red Blood Cell Antigen Phenotype by DNA Analysis", *Transfusion*, vol. 47, S1, Jul. 2007, 60S-63S.
Hashmi, Ghazala et al., "The BeadChip System: A Flexible Array Format for Complex Nucleic Acid and Protein Analysis", *Beadchip Molecular Immunohematology: Toward Routine Donor and Patient Antigen Profiling by DNA Analysis*, Springer, Jan. 2011, 17-31.
International Preliminary Report on Patentability for International Application No. PCT/US2014/010735 dated Jul. 23, 2015, 9 Pages.
International Search Report for International Appl. No. PCT/US2014/010735 dated Apr. 16, 2014.

*Primary Examiner* — Eric S Dejong
(74) *Attorney, Agent, or Firm* — Mauriel Kapouytian Woods LLP; Elaine K. Lee; Michael Mauriel

(57) ABSTRACT

In one exemplary embodiment, a computer-implemented method for determining a genetic result from a biological sample is provided. The method includes receiving nucleic acid amplification data of a biological sample, by a processor, from a biological instrument. The method further includes storing translation data, in a memory. The translation data includes a pattern of assay values associated with possible genetic results. The method further includes comparing the translation data with the nucleic acid amplification data, by the processor, to generate the genetic result of the biological sample. Moreover, the method includes displaying the genetic result, on a display, to a user.

18 Claims, 9 Drawing Sheets

Blood donation qualification process. The donor's blood–stored in the blood bank–and receiver's blood are typed for a better matching to avoid transfusion adverse reactions.

Comparison of blood group phenotyping and extended genotyping strategies.

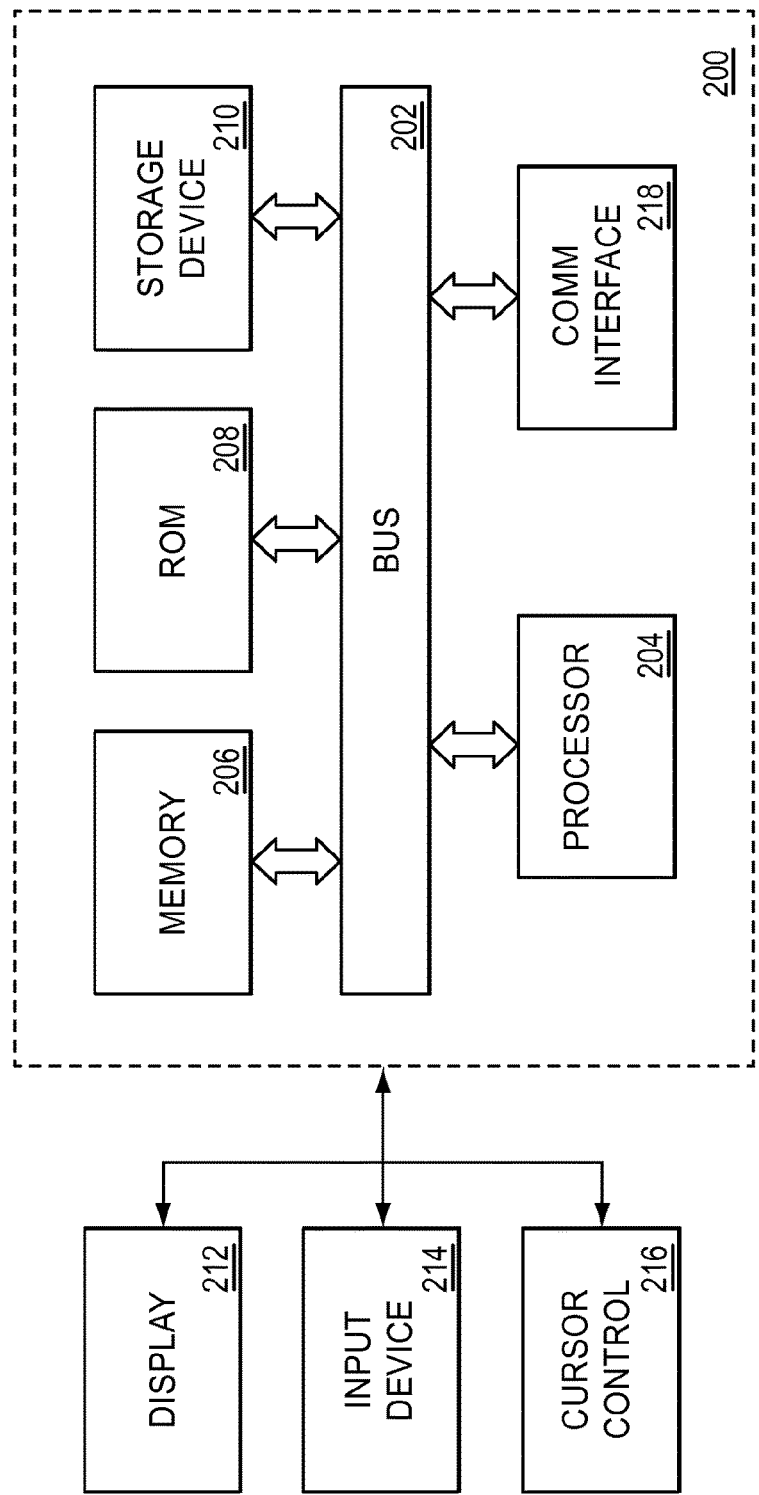

Sample Data

Taqman Genotyper files

HEA14-15-18-20-23-24_20...
Exported By: GUEST
Exported Date:
Software Version: N/A

| # | Sample Name | Assay ID | NCBI SNP | Call | Manual | Task | Well | Experiment Nan |
|---|---|---|---|---|---|---|---|---|
| 60... | ML12-0149 | AHY94E5 | rs8176058 | G/G | false | Unknown | D3e7 | HEA24.spd |
| 60... | ML09-1065 | AHY94E5 | rs8176058 | G/G | false | Unknown | D4e7 | HEA24.spd |
| 60... | ML09-1065 | AHY94E5 | rs8176058 | G/G | false | Unknown | D5e7 | HEA24.spd |
| 60... | ML09-1065 | AHY94E5 | rs8176058 | G/G | false | Unknown | D6e7 | HEA24.spd |
| 60... | ML10-1028 | AHY94E5 | rs8176058 | G/G | false | Unknown | D7e7 | HEA24.spd |
| 60... | ML10-1028 | AHY94E5 | rs8176058 | G/G | false | Unknown | D9e7 | HEA24.spd |

CopyCaller files cnv export.txt
Analysis Software: CopyC...
Plate Type: null
Run Date:
Operator: null

| # | Sample Name | Assay ID | Copy Number |
|---|---|---|---|
| 1 | IHWG9048_2 | C4A | 2 |
| 2 | IHWG9060_4 | C4A | 5 |
| 3 | IHWG9065_2 | C4A | 2 |
| 4 | IHWG9098_2 | C4A | 2 |
| 5 | NKN16010 | C4A | 1 |
| 6 | NKN16027 | C4A | 2 |

Instructions: Some message here.

| | |
|---|---|
| File Edit View History Bookmarks Tools Help | |
| ☐ Project Details | x ☐ Meta-Genotyper x + |
| ⊙ localhost:8080/pgx/app/Pgx_EditProject.htm?projectID=1353D17750171 | ☆ ▽ ⌄ⅽ Y! ▾ Yahoo |
| ◯ YTD ◯!▾ Yahoo ▾ Search ✧ ⊞ Download Youtube ⊟ Amazon eBay Coupons▾ ● Radio ⊞ E ⊞▾ ※ Options▾ | | meta-genotyper
by *life* technologies™

〈 ① Project · Project2012-11-15 14:15:50 ② Setup ③ Data ④ Results 〉

Results                                                                    🔍    ⇧ Export  ⋵Genetic Patterns

| Sample Name | bloodtype | Notes |
|---|---|---|
| C5_5 | Co(a+b-),Cra-,Hy+/Hy-,Js(a-b+),kk,Jk(a-b+),Kn(a+b-),Sc(a+b-),Yt(a+b-),Fy(a+b-),Di(a+b+),Di(a-b-),LW(a+b-),Kp(a+b-),Kp(a+b+),Lu(a+b+),Lu(a-b+),LW(a+b-),Lu(a+b+),Lu(a-b+),M+N+S+s+,M+N-S+s,M+N+S+s,M-N+S+s+,M+N+S+s,M-N+S+s+} | no usable results for these assays: AHCS2MS,AHGJW5G,AHY94E6,AHX058Y,AHLJPUC, AHNTL... |
| ML11-0100 | Co(a+b-),Cra-,Do(a-b+),Hy-,Joa+,Js(a-b+),kk,Jk(a-b+),Kn(a+b-),LW(a+b-),Sc(a+b-),Yt(a+b+),Fy(a+b-),{Di(a+b+),Di(a-b+),Kp(a+b-),Kp(a+b+),Kp(a-b+),Fy(a+b-),Lu(a+b+),Lu(a-b+),M+N-S+s+,M+N+S+s+,M+N-S+s,M-N... | no usable results for these assays: AHCS2MS,AHGJW5G,AHX058Y,AHLJPUC,AHN1L6S,AHI... replicates for these assays:AHWR72Q,inconsistent replicates for these assays:AHWR72Q |
| ML12-0034 | Co(a+b-),Cra-,Do(a-b+),Hy-,Joa+,Js(a-b+),kk,Jk(a-b+),Kn(a+b-),LW(a+b-),Sc(a+b-),Yt(a+b-),Fy(a+b-),{Di(a+b+),Di(a-b+),Di(a+b+),Kp(a+b-),Kp(a+b+),Kp(a-b+),Lu(a+b+),Lu(a-b+),M+N-S+s+,M+N+S+s+,M-N-S+s+,M+N-S+s+,M+N+... | no usable results for these assays: AHCS2MS,AHGJW5G,AHX058Y,AHLJPUC,AHN1L6S,AHI1... |
| ML11-0452B | Co(a+b-),Cra-,Do(a-b+),Hy-,Joa+,Js(a-b+),Jk(a-b+),Kn(a+b-),LW(a+b-),Sc(a+b-),Yt(a+b-),Fy(a+b-) | no usable results for these |

Instructions: Some message here.

| Sample | Rh* Predicted Phenotype | Kell Predicted Phenotype | Kidd Predicted Phenotype | Duffy Predicted Phenotype | MNS Predicted Phenotype | Lutheran Predicted Phenotype | Diego Predicted Phenotype | Colton Predicted Phenotype | Dombrock Predicted Phenotype | Landsteiner-Wiener Predicted Phenotype | Scianna Predicted Phenotype |
|---|---|---|---|---|---|---|---|---|---|---|---|
| Sample 1 | DcEe | Kk, Kp(a-b+), Js(a-b+) | Jk(a+b-) | Fy(a+b+) | Ns | Lu(a-b+) | Di(a+b+) | Co(a+b+) | Do(a-b+)Jo(a)+Hy+ | LW(a+b-) | Sca/Scb- |
| Sample 2 | Dce | kk, Kp(a-b+), Js(a+b+) | Jk(a+b-) | Fy(a+b-) | MNs | Lu(a-b+) | Di(a-b+) | Co(a+b-) | Do(a+b+)Jo(a)+Hy+ | LW(a+b-) | Sca/Scb- |
| Sample 3 | Dce | kk, Kp(a+b+), Js(a-b+) | Jk(a+b-) | Fy(a-b-) | MNs | Lu(a-b+) | Di(a-b+) | Co(a+b-) | Do(a-b+)Jo(a)+Hy+ | LW(a+b-) | Sca/Scb- |
| Sample 4 | Dce | kk, Kp(a-b+), Js(a-b+) | Jk(a+b+) | Fy(a+b-) | NSs | Lu(a-b+) | Di(a-b+) | Co(a+b-) | Do(a+b+)Jo(a)+Hy+ | LW(a+b-) | Sca/Scb- |
| Sample 5 | Dce | kk, Kp(a-b+), Js(a-b+) | Jk(a+b+) | Fy(a-b+) | MSs | Lu(a-b+) | Di(a-b+) | Co(a+b-) | Do(a-b+)Jo(a)+Hy- | LW(a+b-) | Sca/Scb- |
| Sample 6 | Dce | kk, Kp(a-b+), Js(a-b+) | Jk(a+b+) | Fy(a-b+) | Ms | Lu(a-b+) | Di(a-b+) | Co(a+b-) | Do(a+b+)Jo(a)+Hy+ | LW(a+b-) | Sca/Scb- |
| Sample 7 | Dce | kk, Kp(a-b+), Js(a-b+) | Jk(a-b+) | Fy(a+b+) | MNSs | Lu(a+b+) | Di(a-b+) | Co(a+b-) | Do(a-b+)Jo(a)-Hy+ | LW(a+b-) | Sca/Scb- |
| Sample 8 | Dce | kk, Kp(a-b+), Js(a-b+) | Jk(a+b+) | Fy(a+b+) | Ns | Lu(a-b+) | Di(a-b+) | Co(a+b-) | Do(a+b+)Jo(a)+Hy+ | LW(a+b-) | Sca/Scb- |
| Sample 9 | DcEe | Kk, Kp(a-b+), Js(a-b+) | Jk(a+b+) | Fy(a+b+) | MNs | Lu(a-b+) | Di(a-b+) | Co(a+b-) | Do(a+b+)Jo(a)+Hy+ | LW(a+b-) | Sca/Scb- |
| Sample 10 | Dce | kk, Kp(a-b+), Js(a-b+) | Jk(a+b-) | Fy(a+b-) | Ms | Lu(a-b+) | Di(a-b+) | Co(a+b-) | Do(a+b+)Jo(a)+Hy+ | LW(a+b-) | Sca/Scb- |
| Sample 11 | DcEe | kk, Kp(a-b+), Js(a-b+) | Jk(a-b+) | Fy(a+b+)weak | MSs | Lu(a-b+) | Di(a-b+) | Co(a+b+) | Do(a+b+)Jo(a)+Hy+ | LW(a+b-) | Sca/Scb- |
| Sample 12 | DcEe | kk, Kp(a-b+), Js(a-b+) | Jk(a+b-) | Fy(a-b+) | MSs | Lu(a-b+) | Di(a-b+) | Co(a+b-) | Do(a+b+)Jo(a)+Hy+ | LW(a+b-) | Sca/Scb- |
| Sample 13 | Dce | kk, Kp(a-b+), Js(a-b+) | Jk(a+b+) | Fy(a+b+) | MNSs | Lu(a-b+) | Di(a-b+) | Co(a+b-) | Do(a+b+)Jo(a)+Hy+ | LW(a+b-) | Sca/Scb- |
| Sample 14 | Dce | kk, Kp(a-b+), Js(a-b+) | Jk(a-b+) | Fy(a+b-) | Ms | Lu(a-b+) | Di(a-b+) | Co(a+b-) | Do(a+b+)Jo(a)+Hy+ | LW(a+b-) | Sca/Scb- |
| Sample 15 | Dce | kk, Kp(a-b+), Js(a-b+) | Jk(a-b+) | Fy(a+b-) | Ms | Lu(a-b+) | Di(a-b+) | Co(a+b-) | Do(a+b+)Jo(a)+Hy+ | LW(a+b-) | Sca/Scb- |
| Sample 16 | DcEe | Dce | kk, Kp(a-b+), Js(a-b+) | Jk(a+b-) | Fy(a+b-) | Ns | Lu(a-b+) | Di(a-b+) | Co(a+b-) | Do(a+b+)Jo(a)+Hy+ | LW(a+b-) | Sca/Scb- |
| Sample 17 | Dce | kk, Kp(a-b+), Js(a-b+) | Jk(a+b+) | Fy(a+b-) | MNs | Lu(a-b+) | Di(a-b+) | Co(a+b-) | Do(a+b+)Jo(a)+Hy+ | LW(a+b-) | Sca/Scb- |
| Sample 18 | Dce | kk, Kp(a-b+), Js(a-b+) | Jk(a+b+) | Fy(a+b-) | MNs | Lu(a-b+) | Di(a-b+) | Co(a+b-) | Do(a+b+)Jo(a)+Hy+ | LW(a+b-) | Sca/Scb- |
| Sample 19 | Dce | kk, Kp(a-b+), Js(a-b+) | Jk(a+b+) | Fy(a+b-) | MNs | Lu(a-b+) | Di(a-b+) | Co(a+b-) | Do(a-b+)Jo(a)+Hy+ | LW(a+b-) | Sca/Scb- |
| Sample 20 | Dce | kk, Kp(a-b+), Js(a-b+) | Jk(a+b-) | Fy(a-b+)weak | MNs | Lu(a-b+) | Di(a-b+) | Co(a+b-) | Do(a+b+)Jo(a)+Hy+ | LW(a+b-) | Sca/Scb- |
| Sample 21 | D-/D- | kk, Kp(a-b+), Js(a-b+) | Jk(a+b+) | Fy(a-b+)weak | MNs | Lu(a-b+) | Di(a-b+) | Co(a+b-) | Do(a-b+)Jo(a)+Hy+ | LW(a+b-) | Sca/Scb- |

FIG. 8

METHODS AND SYSTEMS FOR DETERMINING META-GENOTYPES

BACKGROUND

In general, genetic assays typically examine a narrow portion of the information contained in DNA and RNA, the primary molecules of genetic information in living beings. It is increasingly becoming the case that a single genetic assay cannot provide the information needed for a technological objective, for example, blood typing, genetic profiling for drug responsiveness, characterization of stem cell pluripotency, etc. As such, using the information from several genetic assays to determine a final result is often challenging.

As mentioned above, there may be more than one genetic assay needed to perform blood typing, for example. The cells that make up the body's tissues and organs are covered with surface markers, or antigens. The blood group a person belongs to depends on the antigens on the red blood cells.

An antigen is any substance to which the immune system can respond. The antigens found on the body's own cells are known as "self-antigens." These self-antigens are not normally attacked by the body's own immune system. For example, the millions of antigens contained in the membrane of each red blood cell are ignored by the body's own immune system. However, when patients receive blood transfusions of blood from other people, their immune systems will attack any donor red blood cells that contain antigens that differ from their self-antigens. As such, ensuring that the antigens of transfused red blood cells match those of the patient's red blood cells is essential for a safe blood transfusion.

As mentioned above, the antigens expressed on the red blood cell determine an individual's blood group. The main two blood groups are called ABO (with blood types A, B, AB, and O) and Rh (with Rh D-positive or Rh D-negative blood types).

Blood group antigens can be either sugars or proteins. For example, the antigens of the ABO blood group are sugars. In contrast, the antigens of the Rh blood group are proteins. The sugar antigens are produced by a series of reactions in which enzymes catalyze the transfer of sugar units. A person's DNA determines the type of enzymes they have, and, therefore, the type of sugar antigens that end up on their red blood cells. Similarly, a person's DNA holds the information for producing the protein antigens. The RhD gene encodes the D antigen, which is a large protein on the red blood cell membrane. Some people have a version of the gene that does not produce D antigen, and therefore the RhD protein is absent from their red blood cells.

Mixing of blood may occur during blood transfusions as well as during labor when a small amount of fetal blood may enter the mother's circulation. As such, it is important to be able to determine blood type to determine immune compatibility.

SUMMARY

In one exemplary embodiment, a computer-implemented method for determining a genetic result from a biological sample is provided. The method includes receiving nucleic acid amplification data of a biological sample, by a processor, from a biological instrument. The method further includes storing translation data, in a memory. The translation data includes a pattern of assay values associated with the desired genetic result. The method further includes comparing the translation data with the nucleic acid amplification data, by the processor, to generate the genetic result of the biological sample. Moreover, the method includes displaying the genetic result, on a display, to a user.

The genetic result may be, but is not limited to, blood type, genetic profiling for drug responsiveness, or characterization of stem cell pluripotency. The pattern of assay values may be, but are not limited to, genotyping, gene expression, copy number, DNA or mRNA sequence assays, for example.

In one exemplary embodiment, a computer-implemented method for determining a genetic pattern from a biological sample is provided. The method includes receiving data containing genetic information from one or more genetic information processing technologies applied to a biological sample. The method further includes storing a map between possible genetic patterns and names for the possible patterns, a meta-genotype, in a memory. The method further includes comparing, by the processor, the genetic pattern from the biological sample with the possible genetic patterns in the map and identifying the meta-genotypes with genetic patterns that are a match or closest match to that of the biological sample. Moreover, the method includes displaying the meta-genotype result, on a display, to a user.

Genetic information processing technologies are generally a combination of genetic assays and the chemical processing procedures and biological instrumentation technologies necessary to perform the genetic assay and generate a result for the assay in electronic form. The genetic information includes the outcome of one or more genetic assays.

In another exemplary embodiment, a non-transitory computer-readable storage medium encoded with processor-executable instructions for determining a meta-genotype from a biological sample is provided. The instructions include instructions for receiving nucleic acid amplification data of a biological sample, by a processor, from a biological instrument. The instructions further include instructions for storing translation data, in a memory. The translation data includes a pattern of assay values associated with meta-genotypes. The method instructions further include instructions for comparing the translation data with the nucleic acid amplification data, by the processor, to generate a meta-genotype result of the sample. Moreover instructions further include instructions for displaying the meta-genotype result, on a display, to a user.

In yet another embodiment, a system for determining a meta-genotype from a biological sample is provided. The system includes a communication interface configured to receive nucleic acid amplification data of a biological sample from a biological instrument. The system further includes a memory configured to store translation data, where the translation data includes a pattern of assay values associated with meta-genotypes. The system also includes a processor configured to compare the translation data with the nucleic acid amplification data to generate a meta-genotype result of the sample. The system includes a display configured to display the meta-genotype result to a user.

DESCRIPTION OF THE FIGURES

FIG. 2 is a block diagram that illustrates a computer system, upon which embodiments of the present teachings may be implemented;

FIG. 5 illustrates an exemplary translator file according to various embodiments described herein;

FIG. 6 illustrates exemplary sample assay data according to various embodiments described herein;

FIG. 7 illustrates an exemplary genetic results display according to various embodiments described herein; and FIG. 8 illustrates another exemplary genetic results display according to various embodiments described herein.

DETAILED DESCRIPTION

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

As mentioned above, it is becoming increasingly the case that a single genetic assay cannot provide the information needed for a technological objective genetic result, for example, blood typing, genetic profiling for drug responsiveness, characterization of stem cell pluripotency, etc. Hence, there is a need to combine the information from several genetic assays. Referring to this combination of genetic information as a genetic pattern, it is useful to be able to assign names to various genetic patterns. Genetic patterns may be referred to as meta-genotypes. By storing and analyzing meta-genotypes, a genetic result may be determined.

Figure 1A:
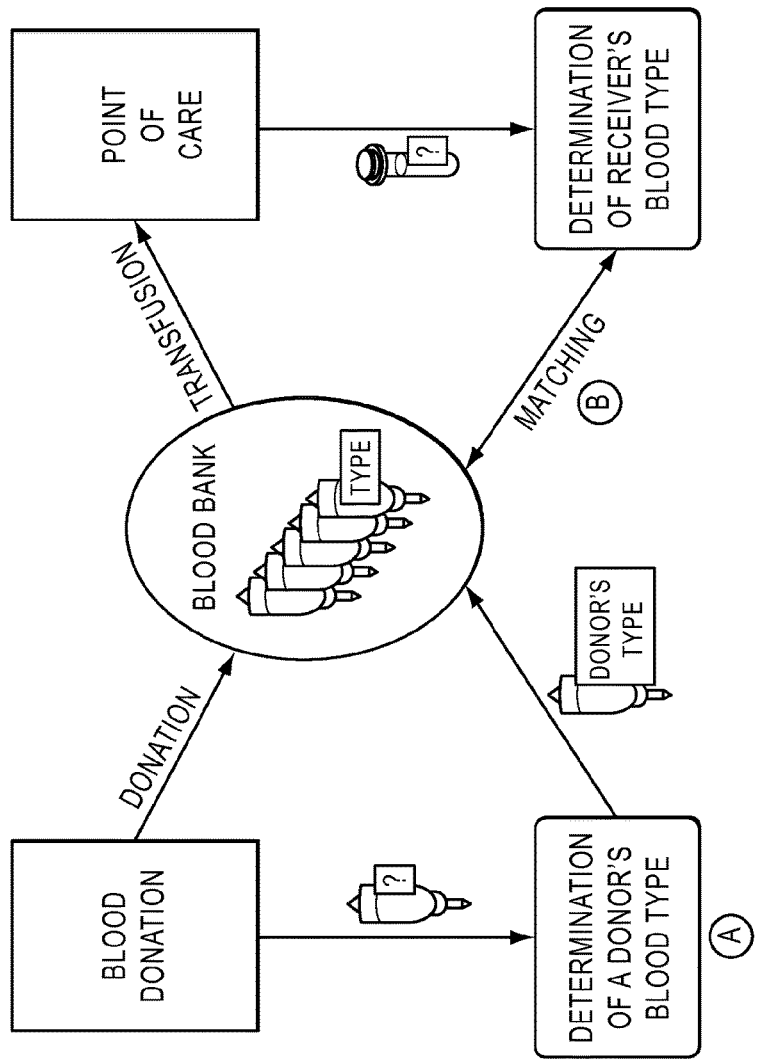
FIG. 1 illustrates an exemplary blood donation qualification process.
Figure 1B:
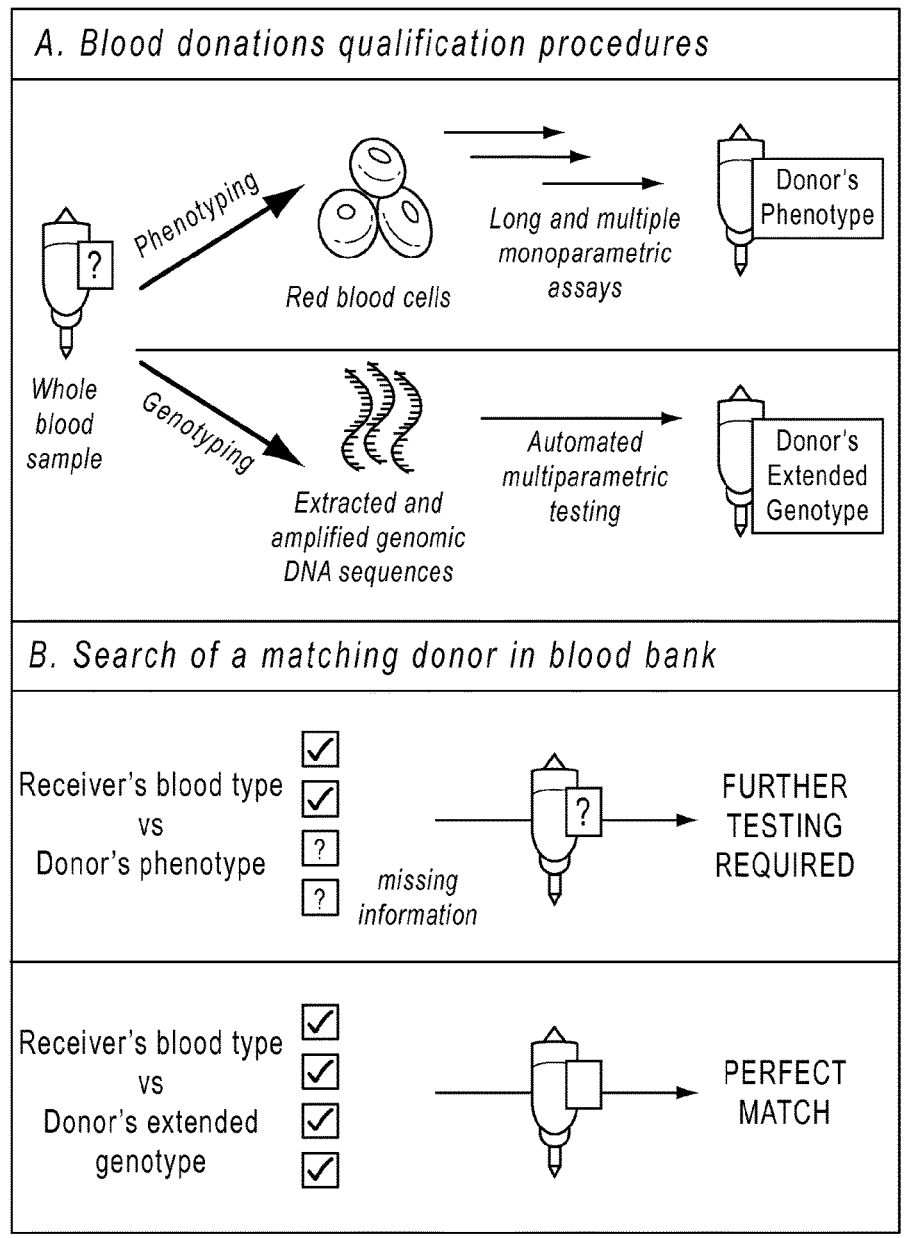

Referring back to the blood typing example, quick and accurate blood typing is important for safe blood transfusions. An example of a blood transfusion process is illustrated in FIG. 1. The donor's blood is stored in the blood bank. The receiver of the blood and the donor blood are typed to avoid transfusion adverse reactions. Furthermore, FIG. 1 also illustrates a comparison of blood group phenotyping and genotyping strategies.

Blood groups can be determined by analyzing a person's DNA to determine variants in a group of genes known to be important in determining blood type. Typing the blood begins with a blood sample. The blood sample can then be processed according to known methods to extract the DNA from the blood cells. The DNA, a polynucleotide chain, is analyzed according to known methods, such as polymerase chain reaction (PCR).

In general, amplification of a target DNA strand by PCR proceeds through a series of temperature regulated cycles using the activity of a thermostable enzyme and a sequence specific primer set. At an appropriate temperature, primers hybridize to portions of the DNA strand and the enzyme successively adds a plurality of nucleotide bases to elongate the primer resulting in the production of progeny (daughter) strands. Each progeny strand possesses a complimentary composition relative to the target strand from which it was derived and can serve as a target in subsequent reaction cycles.

When applying quantitative methods to PCR-based technologies, a fluorescent probe or other detectable reporter construct may be incorporated into the reaction to provide a means for determining the progress of the target amplification. In the case of a fluorescent probe, the reaction can be made to fluoresce in relative proportion to the quantity of nucleic acid product produced. As such, using PCR, assays for nucleotides sequences corresponding to the blood typing genes and gene variants are the target sequences and are used to determine the blood type of the blood sample.

Assays used to determine these gene variants are described in related application U.S. 61/852,355 filed Mar. 15, 2013. For example, described in this application, specific assays were designed for RHD deletion based on distinguishing one and two normal alleles based on copy number assays and VIC/FAM ratio. Further, other assays to determine blood typing genes and gene variants of DNA have been described in published scientific literature.

Although PCR data is used as an example of genetic information data, other genetic information processing technologies may be used to generate genetic information data. Genetic information data may include genotyping, copy number, sequence, and gene expression data.

Analyzing the genetic information data quickly and accurately can be done by a computing system. An exemplary computing system for determining blood type is described below and illustrated in FIG. 2.

Computer-Implemented System

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on non-transitory computer-readable media. Some other processes can be implemented using analog circuitry, as is well known to one of ordinary skill in the art. Additionally, memory or other storage, as well as communication components, may be employed in embodiments of the invention.

FIG. 2 is a block diagram that illustrates a computer system 200 that may be employed to carry out processing functionality, according to various embodiments. Instruments to perform experiments may be connected to the exemplary computing system 200. Computing system 200 can include one or more processors, such as a processor 204. Processor 204 can be implemented using a general or special purpose processing engine such as, for example, a microprocessor, controller or other control logic. In this example, processor 204 is connected to a bus 202 or other communication medium.

Further, it should be appreciated that a computing system 200 of FIG. 2 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 200 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 200 may be configured to connect to one or more servers in a distributed network. Computing system 200 may receive information or updates from the distributed network. Computing system 200 may also transmit information to be stored within the distributed network that may be accessed by other clients connected to the distributed network.

Computing system 200 may include bus 202 or other communication mechanism for communicating information, and processor 204 coupled with bus 202 for processing information.

Computing system 200 also includes a memory 206, which can be a random access memory (RAM) or other dynamic memory, coupled to bus 202 for storing instructions to be executed by processor 204. Memory 206 also may be used for storing temporary variables or other intermediate information during execution of instructions to be executed by processor 204. Computing system 200 further includes a read only memory (ROM) 208 or other static storage device coupled to bus 202 for storing static information and instructions for processor 204.

Computing system 200 may also include a storage device 210, such as a magnetic disk, optical disk, or solid state drive (SSD) is provided and coupled to bus 202 for storing information and instructions. Storage device 210 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 210 may include other similar instrumentalities for allowing computer programs or other instructions or data to be loaded into computing system 200. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 210 to computing system 200.

Computing system 200 can also include a communications interface 218. Communications interface 218 can be used to allow software and data to be transferred between computing system 200 and external devices. Examples of communications interface 218 can include a modem, a network interface (such as an Ethernet or other NIC card), a communications port (such as for example, a USB port, a RS-232C serial port), a PCMCIA slot and card, Bluetooth, etc. Software and data transferred via communications interface 218 are in the form of signals which can be electronic, electromagnetic, optical or other signals capable of being received by communications interface 218. These signals may be transmitted and received by communications interface 218 via a channel such as a wireless medium, wire or cable, fiber optics, or other communications medium. Some examples of a channel include a phone line, a cellular phone link, an RF link, a network interface, a local or wide area network, and other communications channels.

Computing system 200 may be coupled via bus 202 to a display 212, such as a cathode ray tube (CRT) or liquid crystal display (LCD), for displaying information to a computer user. An input device 214, including alphanumeric and other keys, is coupled to bus 202 for communicating information and command selections to processor 204, for example. An input device may also be a display, such as an LCD display, configured with touchscreen input capabilities. Another type of user input device is cursor control 216, such as a mouse, a trackball or cursor direction keys for communicating direction information and command selections to processor 204 and for controlling cursor movement on display 212. This input device typically has two degrees of freedom in two axes, a first axis (e.g., x) and a second axis (e.g., y), that allows the device to specify positions in a plane. A computing system 200 provides data processing and provides a level of confidence for such data. Consistent with certain implementations of embodiments of the present teachings, data processing and confidence values are provided by computing system 200 in response to processor 204 executing one or more sequences of one or more instructions contained in memory 206. Such instructions may be read into memory 206 from another computer-readable medium, such as storage device 210. Execution of the sequences of instructions contained in memory 206 causes processor 204 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 204 for execution. Such instructions, generally referred to as "computer program code" (which may be grouped in the form of computer programs or other groupings), when executed, enable the computing system 200 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 210. Volatile media includes dynamic memory, such as memory 206. Transmission media includes coaxial cables, copper wire, and fiber optics, including the wires that comprise bus 202.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 204 for execution. For example, the instructions may initially be carried on magnetic disk of a remote computer. The remote computer can load the instructions into its dynamic memory and send the instructions over a telephone line using a modem. A modem local to computing system 200 can receive the data on the telephone line and use an infra-red transmitter to convert the data to an infra-red signal. An infra-red detector coupled to bus 202 can receive the data carried in the infra-red signal and place the data on bus 202. Bus 202 carries the data to memory 206, from which processor 204 retrieves and executes the instructions. The instructions received by memory 206 may optionally be stored on storage device 210 either before or after execution by processor 204.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Distributed System

Figure 3:
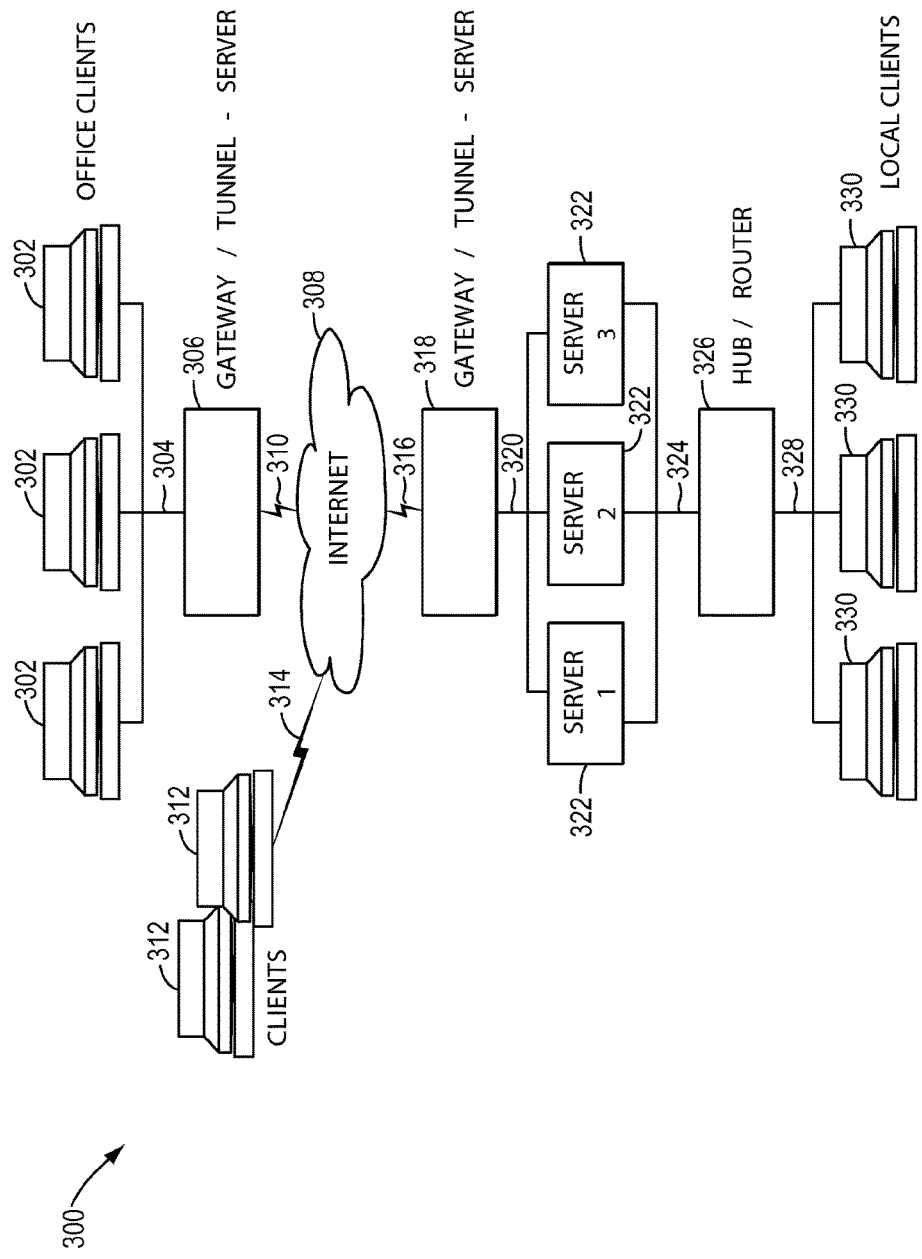
FIG. 3 is a block diagram that illustrates a distributed network system, upon which embodiments of the present teachings may be implemented.

Some of the elements of a typical Internet network configuration 300 are shown in FIG. 3, wherein a number of client machines 302 possibly in a remote local office, are shown connected to a gateway/hub/tunnel-server/etc 310 which is itself connected to the internet 308 via some internet service provider (ISP) connection 310. Also shown are other possible clients 312 similarly connected to the internet 308 via an ISP connection 314, with these units communicating to possibly a central lab or office, for example, via an ISP connection 316 to a gateway/tunnel-server 318 which is connected 320 to various enterprise application servers 322 which could be connected through another hub/router 326 to various local clients 330. Any of these servers 322 could function as a development server for the analysis of potential content management and delivery design solutions as described in the present invention, as more fully described below.

Although various embodiments have been described with respect to certain exemplary embodiments, examples, and applications, it will be apparent to those skilled in the art that various modifications and changes may be made without departing from the present teachings.

Meta-Genotype Analysis

As used herein, SNP genotype means a single nucleotide substitution or a deletion or an insertion where the nucleotide(s) is/are the ones on the 5' to 3' strand; copy number means the number of copies of a gene found within a genome; assay means a set of reagents and a processing protocol to determine the value a specific piece of genetic information, the result of the assay; meta-genotype means a name for a genetic pattern; a genetic pattern is a combination of results from one or more assays.

Referring to the blood typing example, Example 1 (below) shows results from assays for specific blood typing genes and gene variants. The results from these assays indicated that the blood type of the sample is Fy(a+b−).

| Blood Type | C15769614_10 | AH0I2LD | AH39W31 |
|---|---|---|---|
| Fy(a + b−) | T/T | A/G | G/G |

Example 1: Meta-Genotype for Blood Phenotyping

Figure 4:
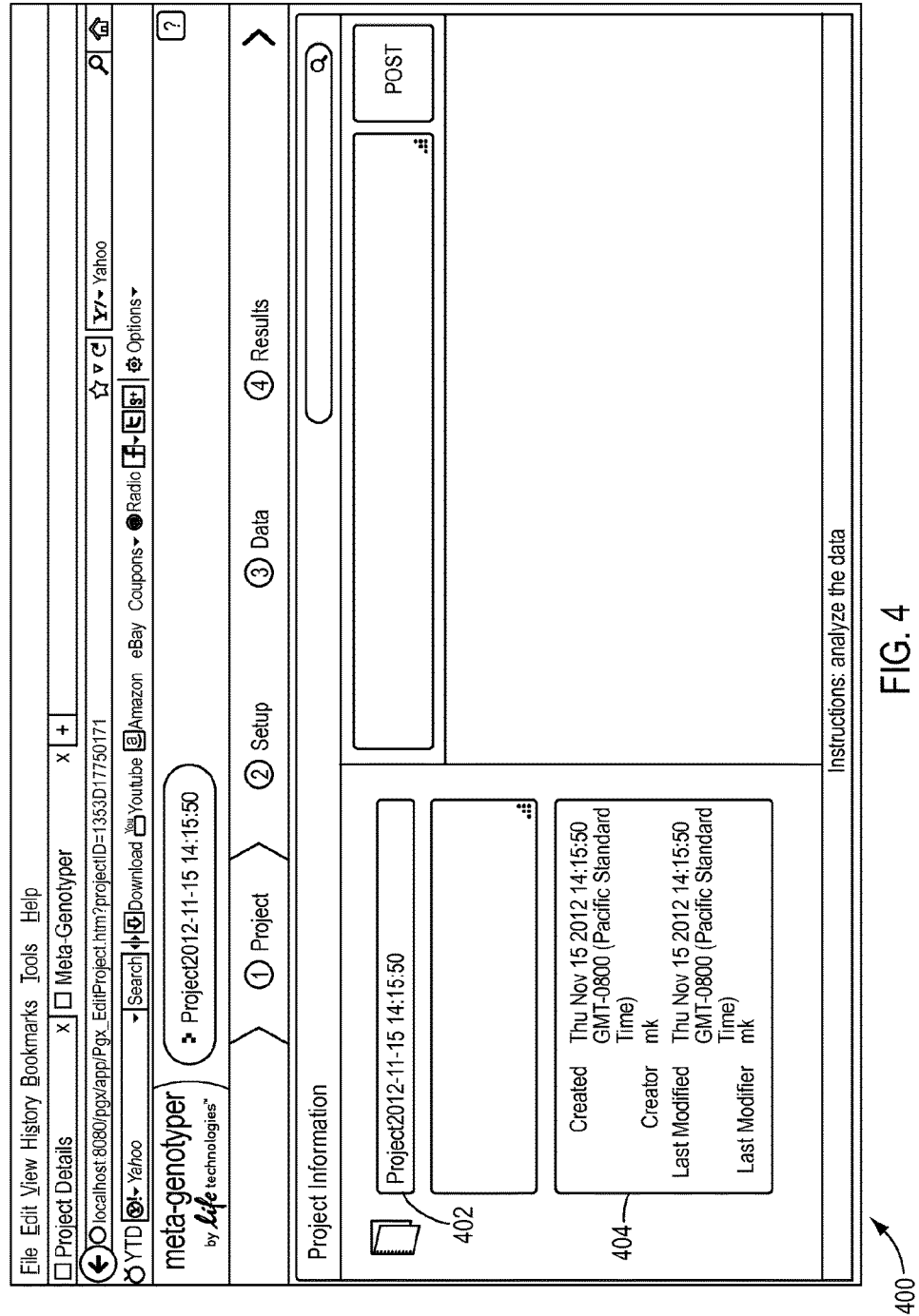
FIG. 4 illustrates an exemplary create project graphical user interface (GUI) according to various embodiments described herein.

A computer-implemented workflow for determining meta-genotype may begin by creating a new project to organize the assay data files for a particular sample. The user interface 400 for creating a project according to various embodiments is depicted in FIG. 4. The create project user interface 400 allows a user to input a name for the project in input box 402 and shows data associated with the project including the date the project was created, the user creating the project, the last modified date and time, and the last user to modify the project, in information box 404, for example. The create project user interface 400 provides a simple way for a user to organize data and track various biological samples.

As described above, the gene genetic pattern of a biological sample is analyzed to determine a meta-genotype. In blood typing, the genes important for typing might be divided into two or more sub-groups. Each sub-group would be associated with a sub-meta-genotype. The full meta-genotype would be the combination of all the sub-meta-genotypes. To analyze the gene genetic pattern, the processor of a computing system compares with known gene genetic patterns which match to a specific meta-genotype of sub-meta-genotype according to various embodiments described herein. The known gene genetic patterns mapped to specific meta-genotypes may be known as translator data.

Translator Data

Figure 5:
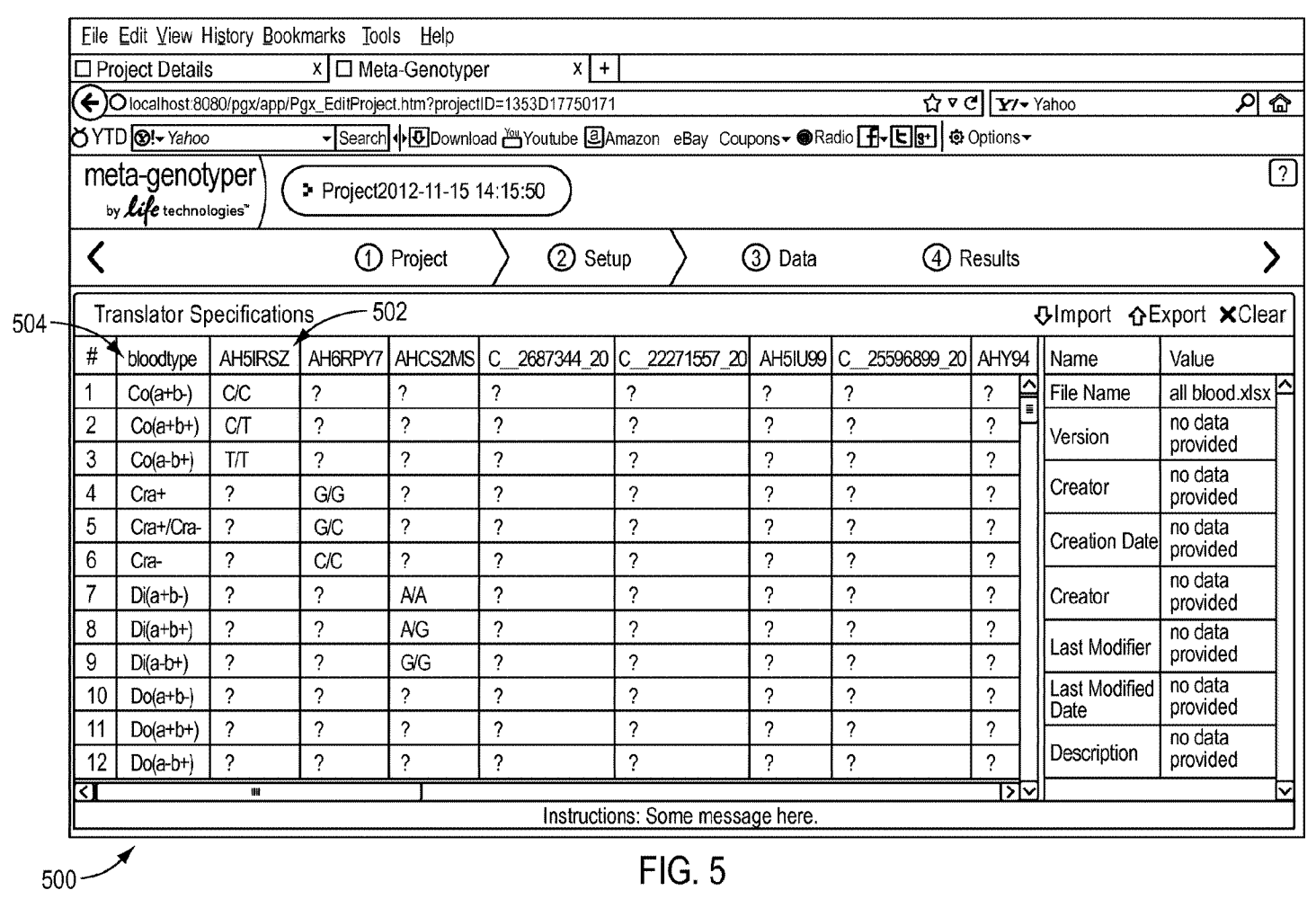

The translator data may be stored in a translator file and stored in the memory of a computing system. FIG. 5 illustrates a translator file that may be loaded to a user's project to translate the data and give the meta-genotype results.

According to various embodiments, a translator file may be a CSV (comma delimited) or TXT (tab delimited) file. Generally, the translator file has two main parts: the header and the translator specification. In one example, the header of the translator file may contain the following fields:

1) Name
2) Version
3) Creator
4) Creation date
5) User name of last person to modify
6) Last modified date
7) Description
8) Any text in rows following the Description field are ignored until "Output" is found in the leftmost column.

The translator file specification includes assay identification and associated values. The translator file may include 1 to 50 assays in some embodiments. In other embodiments, the translator file may include up to 100, 200, or 1000 assays, for example. The assay types are shown in row 502. The patterns of values for meta-genotypes are also included in the translator file to show the result. In this example, the result is a bloodtype. The results are shown in column 504.

According to various embodiments described herein, two kinds of translator files may be used. The first type of translator file is a mono-allelic translator. In this case, the software generates the bi-allelic table. The user can view and export the bi-allelic table. (This will allow users to have the software help them make bi-allelic translators that they can then customize.) The second type of translator file is a Bi-allelic translator. In this case, the user making the translator should generate all possible bi-allelic combinations but is not required to do this. (If the list is not complete there is a possibility that the software will run across a genetic pattern that is not listed in the translator. In this case, it would report the notice "no translation available".) Genetic patterns consistent with missing bi-allelic combinations, if determined by the computer-implemented blood typing method, will be marked as "no translation available" according to one example.

For a mono-allelic translator, each genotype can consist of a single value: A, G, C, T, a string of these four letters, -, ins, del, noamp, Each copy number can consist of a single integer, 0 included. The integer can also be pre-pended with >, <, >=, <=.

For a bi-allelic translator, each genotype can consist of one or two genotypes; in the latter case, the two genotypes are separated by a semicolon. Each genotype is expressed as a bi-allelic pair, the values listed for the mono-allelic translator separated by "/". There can be only one copy number.

If a mono-allelic translator file is loaded, processor-executable instructions, according to various embodiments, converts the mono-allelic translator file into a bi-allelic translator file, shows the conversion, and allows the user to export it. The reasoning is that the user can then customize the bi-allelic translator file and replace the existing one for the project. For example, blood typing people may wish to replace the default bi-allelic notation (generated by the mono- to bi-allelic translator conversion) for the meta-genotype with their customized notation for the meta-genotype. Another example, users may wish to eliminate redundant genetic patterns.

In constructing a bi-allelic translator from a mono-allelic translator, all possible combinations of meta-genotypes called out in the mono-allelic translator are added to the bi-allelic translator. The combining rules are set up to generate biologically/experimentally meaningful results. For example, for copy number assays, the copy numbers called out in the mono-allelic translator are added to determine the copy number value for the bi-allelic translator. For SNP genotyping assays, the mono-allelic haplotype values are combined into a diplotype; combining with a noamp haplotype value results in a homozygous diplotype.

Meta-genotypes can be grouped by giving meta-genotypes group labels. Assays can be grouped by giving assays group labels.

In constructing a bi-allelic translator from a mono-allelic translator when grouping is present, combinations of meta-genotypes can be restricted to be formed within meta-genotype group.

In constructing a bi-allelic translator from a mono-allelic translator, blank cells in the mono-allelic translator are interpreted as possibly taking on any value for the corresponding assay except for when there is no amplification. The possible values for an assay can be determined by examining all values listed in the mono-allelic translator for that assay across all meta-genotypes. In various embodiments, this can be restricted to meta-genotype group.

In a bi-allelic translator, a blank cell means that the corresponding assay is not relevant for the corresponding meta-genotype; i.e., for that meta-genotype/assay combination, the assay result can be any value.

In various embodiments, a translator may contain non-unique meta-genotypes as well as non-unique genetic patterns. Alternatively, a translator may be restricted to have unique meta-genotypes or unique genetic patterns or both.

In various embodiments, the values that can be assigned to a given meta-genotype/assay combination is determined by what is appropriate for the assay. For example, SNP genotype assays A,G,C,T, any string of these letters, NOAMP for no amplification, "-" for the normal allele of an indel assay when "del" or "ins" is used to indicate the presence of the insertion or deletion, "del" for a deletion, "ins" for an insertion. For copy number assays, any integer >=0 possibly prepended by <, >, <=, >=. For gene expression assays, the appropriate values could be a fold change interval or a fold change threshold or some other metric of gene expression. For sequencing assays, the value can be a specific sequence of IUB codes.

Translators can be constructed to detect impossible genetic patterns. For example, a meta-genotype "impossible01" can be assigned to a genetic pattern that is physically impossible. An example of a physically impossible genetic pattern is SNP genotyping assays where one assay, assay1, detects the presence or absence of a deletion while another assay, assay2, detects an allele that is a variant within the deletion. An impossible genetic pattern, in this example, would be the presence of a homozygous deletion from assay1 while assay2 shows the presence of one of its alleles. If assay1 is correct, assay2's result should be noamp.

In various embodiments, the translator file may be pre-loaded into the memory or may be uploaded from a removable memory or transmitted over a network. In various embodiments, the translator file may be updated and retransmitted to the computing system to update the translator. According to various embodiments, the software provides version tracking, all export files will record the version of the translator used to create the exported results.

Users may manage translator files on their own; e.g., restricting access to them, validating their integrity, version labeling and control, etc. Users may also want to make sure that the correct version of a translator is loaded.

The computing system implementing the meta-genotyping method may also include processor-executable instructions for error checking the translator. For example, the error checking instructions may include checking the following for an embodiment that only included SNP genotyping assays and copy number assays:

1. All IDs identifying assays must be unique, no repeats.
2. All genotype values must be from the set of possibilities that are generated by TaqMan Genotyper with the addition of "ins" and "del". Specifically, only these values are allowed: A,G,C,T, any string of these letters, "/" as separator between alleles, NOAMP for no amplification, "-" for the normal allele of an indel assay when "del" or "ins" is used to indicate the presence of the insertion or deletion, "del" for a deletion, "ins" for an insertion (and any capitalization). Any other call in a translator is considered invalid.
3. All genotype and meta-genotype values must have "/" for a bi-allelic translator (except for blank entries); none should have the "/" for a mono-allelic translator.
4. Copy numbers must be integral including 0.
5. Copy numbers can be pre-pended by <, >, <=, or >=.
6. For mono-allelic translators, only one value is allowed per cell of the table (contrast to bi-allelic translators) (This is mainly to simplify translation to a bi-allelic translator.)
7. For bi-allelic translators, one or two values are allowed for genotypes where values are separated by semicolons, only one value is allowed for copy numbers.
8. The genetic pattern must have at least 1 assay.
9. The genetic pattern can have at most N assays where an example of N is 50.
10. Error messages for problem translator files should show problem values (at least one value where applicable).
11. Any genotyping assay can have only two unique values in the translator in addition to blank and noamp. (A genotyping assay is assumed to probe two alleles.) This means that across meta-genotypes, only two allele identifiers are found (A, G, C, T, unique sequences of these, ins, del, and/or -).
12. Any genotyping assay must have two unique values in the translator excluding blank 13. Any genotyping assay with "del" or "ins", capitalization irrelevant, must be paired with "-".

Sample Assay Data

In addition to the translator file, the computing system for determining meta-genotypes, according to various embodiments, requires sample assay data. An example of sample assay data with SNP genotype and gene copy number data is depicted in FIG. 6. Sample assay data may be, but is not limited to, nucleic acid amplification data (shown in FIG. 6, sequencing data, copy number data, gene expression data, and genotyping data, according to various embodiments. Sample assay data may be any piece of genetic information data.

According to various embodiments, the genetic information for a given sample are collected from a plurality of assays. If there are multiple results for the same assay, the processor-executable instructions implemented on the computing system considers them to be replicates and consensus is required for the result to be assigned for that assay and sample combination. Non-consensus situations are flagged and the result for that sample/assay combination is considered undetermined.

For each sample, the computing system implementing the meta-genotyping method searches for the match(es) between a sample's genetic pattern and those listed in the translator file to determine the meta-genotype(s). For assay results that are not enumerated, i.e., for continuous valued results, matches can be made by dividing the continuous results into categories using one or more thresholds, for example.

Results

Meta-genotype results are generated and displayed, for each sample and each meta-genotype group. An example of a meta-genotype result display 700 is depicted in FIG. 7. Another example of meta-genotype result display 800 is depicted in FIG. 8. The meta-genotype results may include all the meta-genotypes that match its genetic pattern, including alternative meta-genotypes when a meta-genotype cannot be uniquely determined (which is the case when there is missing data or undetermined results for one or more assays that are needed by a given meta-genotype) and generates notes on samples for which there are special circumstances such as missing or undetermined values, assay results manually assigned by a human reviewer, etc. The following fields can be exported for each sample: sample ID, meta-genotype, notes reporting special circumstances (these are the "flags"). Other information to export: translator file used, date of last modification to the translator, translator version number, input data file names and creation dates for these files.

In various embodiments, uniquely determined meta-genotypes are visibly distinguishable from non-uniquely determined meta-genotypes (possible alternative meta-genotypes) in reports.

There may be cases where exception handling is needed. An example from SNP genotyping assays: A noamp result may usually be interpreted as a undetermined value for an assay. However, if noamp is explicitly listed in a translator as a possible outcome, an exact match of noamp between the genetic pattern for a biological sample and the genetic pattern in the translator would be required. On top of this exception, if the noamp value in the genetic pattern of the biological sample causes no matches to be found with the genetic patterns in the translator, the genetic pattern of the biological sample is re-analyzed after noamp is replaced by undetermined. In various embodiments, the genetic pattern of a biological sample may be run through the translator multiple times where the outcome of each pass determines one or more modifications to the genetic pattern before comparing with the genetic patterns of the translator again.

After initial results are generated and displayed, at a later time, additional data can be loaded and data currently in the project can be removed. The updated data is analyzed and the updated results are displayed to the user. Furthermore, the translator file can be replaced. This also triggers the data to be analyzed when the user goes to view results or export results.

EXAMPLE

To further explain the embodiments described herein, an abstract simplified example is described below. In this example, suppose genes K, J, L, and M are important. Also suppose that the following particular variations of these genes are important: K1, K2, K3, J1, J2, J3, L2, L6, L7, L8, M1, M2, M3. The assays used will have been designed to determine, for each gene of interest, which variant is present in the biological sample. Suppose this turned out to be K1, J3, L7, and M3. So our genetic pattern is "K1 J3 L7 M3".

Further, suppose there are two sub-groups: gene K and J are in group one, gene L and M are in group 2.

Suppose we have these sub-meta-genotypes for group one:

| Sub-Meta-genotype | Gene K variant | Gene J variant |
|---|---|---|
| typeA | K1 | J3 |
| typeB | K3 | J1 |
| typeAB | K2 | J2 |
| typeC | K1 | J1 |

Suppose we have these sub-meta-genotypes for group two:

| Sub-meta-genotype | Gene L variant | Gene M variant |
|---|---|---|
| positive | L7 | M3 |
| negative | L2 | M1 |

Thus, the full meta-genotype results in our example is "typeA positive".

Note that our example does not list all possible combinations of the variants for brevity. But it is also not necessary to do so since a certain genetic pattern may have never been observed. In this case, if our biological sample had a genetic pattern that was not listed in the tables the software would signal that no mapping to a meta-genotype is available.

Handling Incomplete Information

If there is incomplete information, the software identifies all the meta-genotypes that are consistent with the available information. These meta-genotypes are shown as possible alternative meta-genotypes. Extending our example, suppose our genetic pattern is "K1 UND L7 M3" where UND signals that the result for gene J is not determined (maybe data is missing or step (3) failed for gene J for some reason. In this case, reading from the tables above, these are the meta-genotypes consistent with the available data: "typeA positive" and "typeC positive"

Although various embodiments have been described with respect to certain exemplary embodiments, examples, and applications, it will be apparent to those skilled in the art that various modifications and changes may be made without departing from the present teachings.

What is claimed is:

1. A computer-implemented method for determining a genetic result from a biological sample, the method comprising:
   storing a translation file in a computer memory, the translation file including a plurality of associations between a plurality of assays and a plurality of configured meta-genotypes;
   receiving at a processor, nucleic acid amplification readings from a biological instrument applying the plurality of assays to the biological sample, wherein the biological sample comprises a blood sample;
   applying the translation file at the processor to transform the nucleic acid amplification readings into a visualization on a computer display;
   wherein the visualization comprises a plurality of assigned meta-genotypes for the plurality of assays applied to the biological sample, wherein the assigned meta-genotypes comprise blood types, including alternative meta-genotypes for a subset of the plurality of configured meta-genotypes that cannot be uniquely assigned; and an association of visual alerts with the assigned meta-genotypes transformed from assays having missing or undetermined values.

2. The computer-implemented method of claim 1, wherein the nucleic acid amplification readings comprise polymerase chain reaction readings.

3. The computer-implemented method of claim 1, wherein the assays indicate presence or absence of blood typing genes and gene variants, wherein a pattern of values of one or more assays corresponds to one or more of the blood types.

4. The computer-implemented method of claim 1, wherein the translation file includes a plurality of patterns of assay values associated with the blood types.

5. The computer implemented method of claim 4, wherein the translation file includes alternative possible blood types associated with the patterns of assay values.

6. The computer-implemented method of claim 3, wherein the visualization further comprises a blood type result, along with at least one alternative possible blood type.

7. A non-transitory computer-readable storage medium encoded with processor-executable instructions for determining a genetic result from a blood sample, wherein the instructions, when executed by a processor, perform:
   storing a translation file in a computer memory, the translation file including a plurality of associations between a plurality of assays and a plurality of configured meta-genotypes;
   receiving at a processor, nucleic acid amplification readings from a biological instrument applying the plurality of assays to the blood sample;
   applying the translation file at the processor to transform the nucleic acid amplification readings into a visualization on a computer display;
   wherein the visualization comprises a plurality of assigned meta-genotypes for the plurality of assays applied to the blood sample, wherein the assigned meta-genotypes comprise blood types, including alternative meta-genotypes for a subset of the plurality of configured meta-genotypes that cannot be uniquely assigned; and an association of visual alerts with the assigned meta-genotypes transformed from assays having missing or undetermined values.

8. The computer-readable storage medium of claim 7, wherein the nucleic acid amplification readings comprise polymerase chain reaction readings.

9. The computer-readable storage medium of claim 7, wherein the assays indicate presence or absence of blood typing genes and gene variants, wherein a pattern of values of one or more assays corresponds to one or more blood types.

10. The computer-readable storage medium of claim 7, wherein the translation file includes a plurality of patterns of assay values associated with the blood types.

11. The computer-readable storage medium of claim 10, wherein the translation file includes alternative possible blood types associated with the patterns of assay values.

12. The computer-readable storage medium of claim 7, wherein the visualization further comprises a blood type result, along with at least one alternative possible blood type result.

13. A system for determining a genetic result from a blood sample, the system comprising:
   a communication interface to receive nucleic acid amplification readings for the blood sample from a biological instrument applying a plurality of assays to the blood sample;
   a memory configured to store a translation file, the translation file including a plurality of associations between the plurality of assays and a plurality of configured meta-genotypes;
   a processor configured to receive the nucleic acid amplification readings from the communication interface and apply the translation file to transform the nucleic acid amplification readings into a visualization on a computer display,
   wherein the visualization comprises a plurality of assigned meta-genotypes for the plurality of assays applied to the blood sample, wherein the assigned meta-genotypes comprise blood types, including alternative meta-genotypes for portions of the nucleic acid amplification readings that cannot be uniquely assigned and an association of visual alerts with the assigned meta-genotypes transformed from assays having missing or undetermined values.

14. The system of claim 13, wherein the nucleic acid amplification readings comprise polymerase chain reaction readings.

15. The system of claim 13, wherein one or more assay values indicate a presence or absence of blood typing genes and gene variants, wherein a pattern of one or more assay values corresponds to one or more of the blood types.

16. The system of claim 13, wherein the translation file comprises a plurality of patterns of assay values associated with a plurality of blood types.

17. The system of claim 13, wherein the translation file comprises alternative possible blood types associated with the patterns of assay values.

18. The system of claim 13, wherein the visualization further comprises one or more of the blood types, along with at least one alternative possible blood type.

* * * * *